United States Patent [19]

Shunichi et al.

[11] 4,070,561
[45] Jan. 24, 1978

[54] METHOD AND APPARATUS OF CONTROLLING AN AUTOMATIC INSPECTION DEVICE

[75] Inventors: Nishizawa Shunichi, Nagaokakyo; Igarashi Taenzi, Kyoto; Fujishima Shigeru, Nagaokakyo, all of Japan

[73] Assignee: Mitsubishi Jukogyo Kabushiki Kaisha, Japan

[21] Appl. No.: 628,324

[22] Filed: Nov. 3, 1975

[30] Foreign Application Priority Data

Nov. 15, 1974 Japan .................. 49-131653

[51] Int. Cl.² ............................ B25J 9/00; F28F 7/00
[52] U.S. Cl. ................................. 364/104; 318/601; 318/603; 214/1 CM; 214/1 BB
[58] Field of Search ............... 214/1 CM, 1 BB; 318/601, 603; 235/92 MP, 151.11

[56] References Cited

U.S. PATENT DOCUMENTS

| | | | |
|---|---|---|---|
| 3,165,680 | 1/1965 | Morrison | 318/603 |
| 3,400,314 | 9/1968 | Wilson | 235/92 MP |
| 3,466,517 | 9/1969 | Leenhouts | 318/603 |
| 3,537,602 | 11/1970 | Cotton et al. | 214/16.4 B |
| 3,889,820 | 6/1975 | Ranger | 214/1 CM |
| 3,913,752 | 10/1975 | Ward et al. | 214/1 CM |
| 3,984,008 | 10/1976 | Syun-ichi et al. | 214/1 BB |
| 4,004,698 | 1/1977 | Gebelin | 214/1 BB |

Primary Examiner—Eugene G. Botz
Attorney, Agent, or Firm—McGlew and Tuttle

[57] ABSTRACT

An automatic inspection device is installed in a field of alignment holes, and the location of the device is shifted, by making use of the holes, by means of a control system in which addresses are assigned to the respective alignment holes, the location of the device is indicated on an objective counter in terms of the address, and a preset counter indicates the shifting direction of the device in terms of the address. In the method, instructions are given to the preset counter and they are compared with the contents of the objective counter, whereupon the device is shifted in the direction of reducing a difference resultant from the comparison. The device is provided with a detector for detection of an obstacle so as to shift the device while avoiding the obstacle.

17 Claims, 14 Drawing Figures

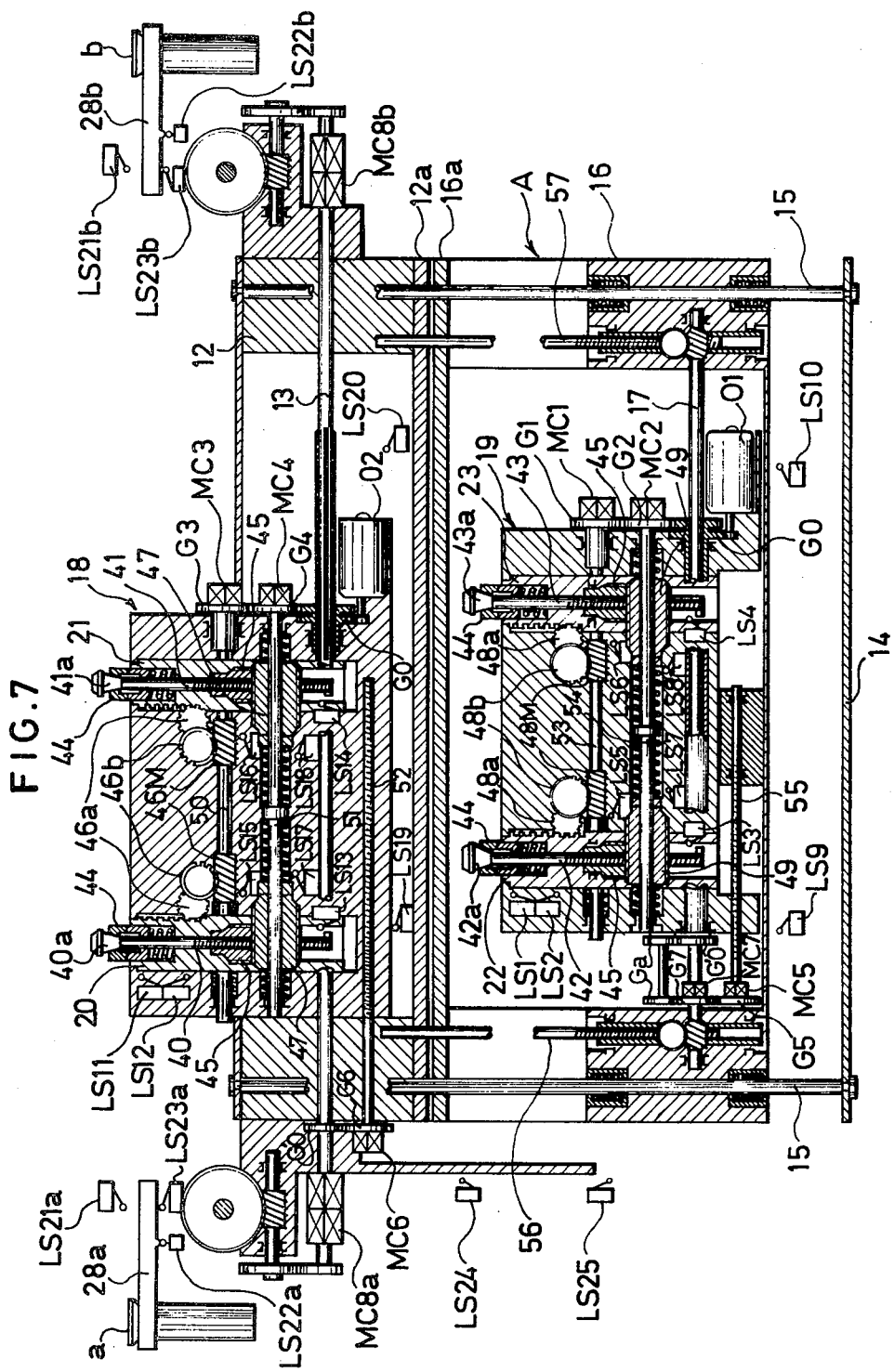

METHOD AND APPARATUS OF CONTROLLING AN AUTOMATIC INSPECTION DEVICE

FIELD AND BACKGROUND OF THE INVENTION

This invention relates to a method of controlling an automatic inspection device for automatically detecting defects in evaporative slender tubes of a steam generator assembled in, for example, a nuclear power plant, and also to an apparatus or system for such control.

It has heretofore been a common practice that, in case where a defect has arisen in any of the evaporative slender tubes of the steam generator of the specified type, a repair man enters the interior of the steam generator through a manhole and inserts a known inspection gauge of the eddy current type or the like from an end port of the evaporative slender tube, secured in a tube sheet or plate at the upper end of a water chamber of the steam generator, into the interior of the evaporative slender tube, thereby to detect the presence of the defect of the evaporative slender tube. As is well known, however, the interior of the steam generator is extremely contaminated by radioactivity. The inspection work in such place is therefore attended with great danger of irradiation. It is accordingly desirable to handle the inspection of the evaporative slender tubes by mechanical means, but such means has not been proposed at present.

SUMMARY OF THE INVENTION

In order to fulfill the need, this invention provides a method of controlling an automatic inspection device in a steam generator defect-detecting automaton or the like wherein defects of evaporative slender tubes of a steam condenser assembled in, e.g., a nuclear power generator are detected by the automatic inspection device which is attached to end ports of the evaporative slender tubes secured in a tube sheet of a water chamber communicating with the tubes, and wherein the position of inspection can be automatically shifted in sequence, and it also provides an apparatus for such control.

The steam generator is installed, for example, plumb. Therefore, the automatic inspection device for detecting the defects of the evaporative slender tubes should preferably be so controlled that it can efficiently inspect the multiplicity of evaporative slender tubes while suspended from the tube end ports at the tube sheet of the water chamber by itself.

To this end, in accordance with the automatic inspection device-controlling method and apparatus of the present invention, addresses are assigned to alignment holes such as evaporative slender tubes; the location of an automatic inspection device is indicated on an objective counter in terms of the address; a preset counter for commanding the shifting direction of the automatic inspection device in terms of the address is provided; when the command of the particular address is given to the preset counter, the particular address is compared with the address of the objective counter, whereupon the inspection device is shifted in the direction of reducing the difference resultant from the comparison; and the inspection device is provided with a detector for detecting an obstacle so that it may shift avoiding the obstacle; whereby the device can be controlled remotely and automatically, and besides, the location of the device can be confirmed.

The above-mentioned object and feature and other particulars of this invention will be more clearly understood from the following detailed description of the preferred embodiments taken with reference to the accompanying drawings.

BRIEF DESCRIPTION OF THE DRAWINGS

In the drawings:

FIG. 7 is a view for conceptually explaining a drive system of the automatic inspection device.

DESCRIPTION OF THE PREFERRED EMBODIMENTS

Figure 1:
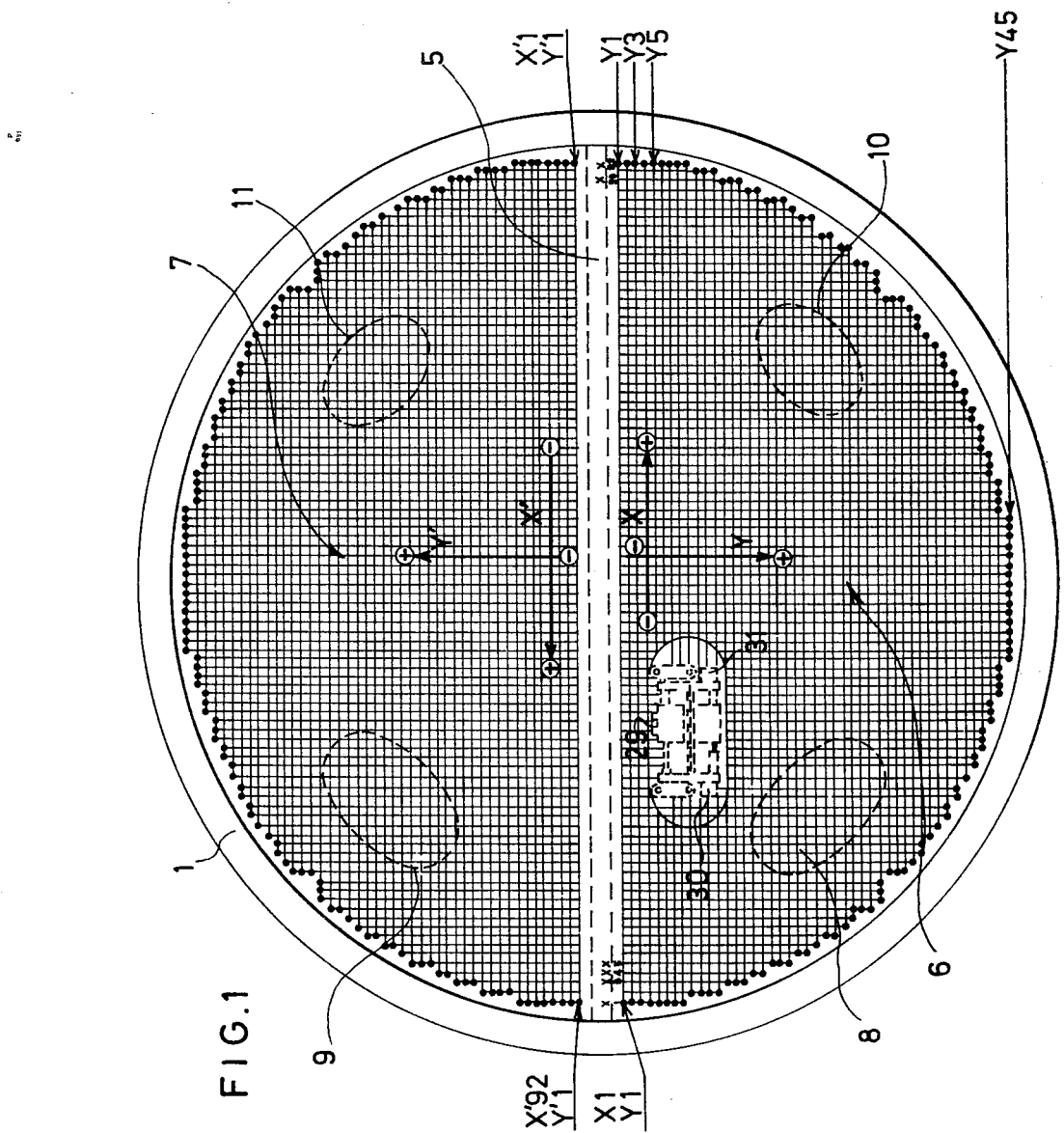
FIG. 1 is a plan view showing a tube sheet of a steam generator.
Figure 2:
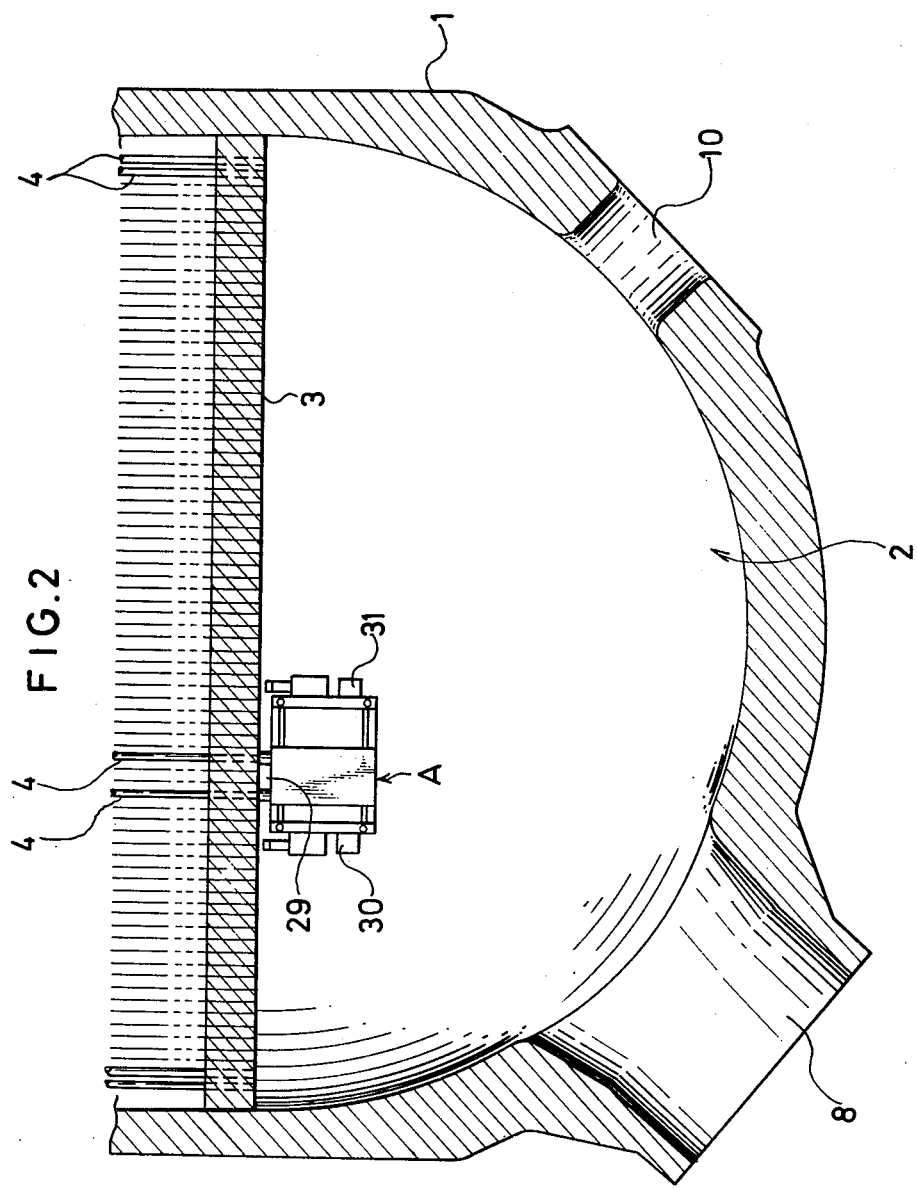
FIG. 2 is a conceptual vertical sectional side elevation showing a water chamber of the steam generator.

In FIGS. 1 and 2, numeral 1 designates a water chamber wall or housing of a steam generator. In a water chamber 2, a tube sheet 3 is disposed. A large number of alignment holes, for example, evaporative slender tubes 4, . . . . are secured to the tube sheet 3 under the state under which their end ports are even with the lower surface of the tube sheet. (In FIG. 1, the points of intersection between vertical lines and horizontal lines indicate the positions of the apertures of the slender tubes 4.) Further, in the water chamber 2, a partition wall 5 is provided so as to divide the interior in two in the vertical direction. That is, the interior of the water chamber is divided into a primary steam feed side 6 and a primary steam discharge side 7 by the partition wall 5. Steam on the feed side 6 is introduced into the water chamber 2 on the discharge side 7 through the slender tubes 4 which are mounted on the tube plates 3 on the feed side 6. As regards the paths of the steam flowing through the individual slender tubes 4, the steam which enters from the end port of the slender tube 4 mounted on the tube sheet 3 on the feed side 6 arrives infallibly at the end port of that slender tube 4 on the discharge side 7 which is situated symmetrically with respect to the partition wall 5. The water chamber wall 1 is formed with a feed port 8 and a discharge port 9 for the primary steam. The feed port 8 communicates with the water chamber 2 on the feed side 6, while the discharge port 9 communicates with the water chamber 2 on the discharge side 7. Adjacent to the feed port 8 and the discharge port 9, a feed side man way 10 and a discharge side man way 11 are formed as worker's entrance and exit for maintenance etc., respectively. X - Y and X' - Y' coordinates are set on the feed side 6 and discharge side 7 of the tube plate 3. The end ports of the slender tubes 4, . . . are given addresses of the coordinate systems, $$\left\{ \begin{matrix} X & 1 \\ Y & 1 \end{matrix} \right\}, \left\{ \begin{matrix} X & 2 \\ Y & 2 \end{matrix} \right\} \ldots \text{and} \left\{ \begin{matrix} X & i \\ Y & j \end{matrix} \right\}$$

(where, in this embodiment, $i$ and $j$ are integers which satisify $1 \leq i \leq 92$ and $1 \leq j \leq 45$) and $$\left\{ \begin{matrix} X' & 1 \\ Y' & 1 \end{matrix} \right\}, \left\{ \begin{matrix} X' & 2 \\ Y' & 2 \end{matrix} \right\} \ldots \text{and} \left\{ \begin{matrix} X' & i \\ Y' & j \end{matrix} \right\}$$

(where, in this embodiment, $i$ and $j$ are integers which meet $1 \leq i \leq 92$ and $1 \leq j \leq 45$).

Figure 3:
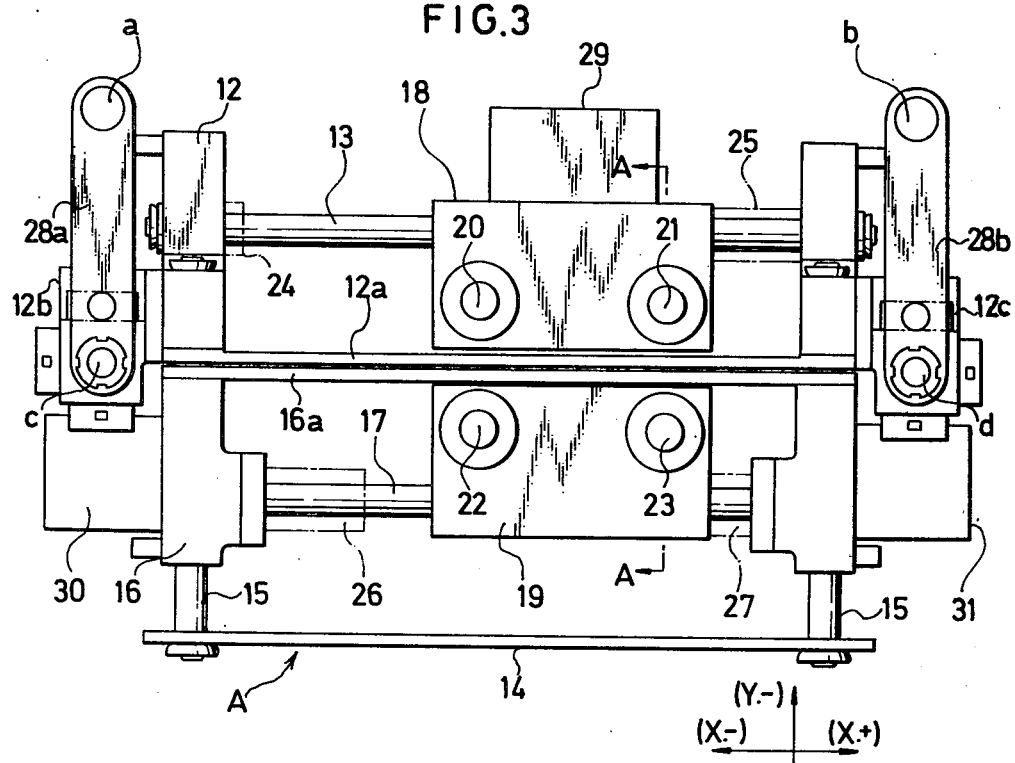
FIG. 3 is a plan view of an automatic inspection device.
Figure 4:
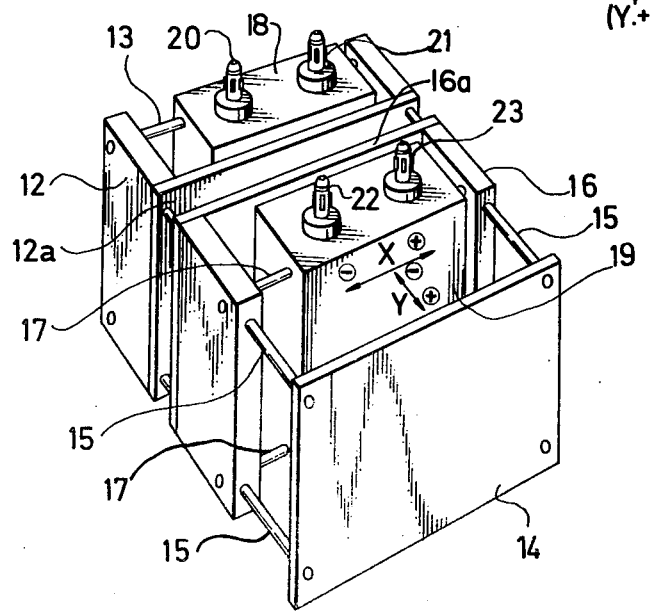
FIG. 4 is a conceptual perspective view of the device shown in FIG. 3.

Inside the steam generator water chamber 2 constructed as stated above, an automatic inspection device, for example, steam generator defect-detecting automaton A, is installed at the end ports of the slender tubes 4 secured in the tube sheet 3. As indicated in FIG. 3, the device A is constructed so that it can move in four directions of (X, +), (X, −), (Y, +) and (Y, −). In FIGS. 3 and 4, numeral 12 designates a frame on the (Y, −) side. When viewed from above, the frame 12 is U-shaped in section. The frame 12 is provided with a back plate 12a on its side facing inward of the device A, and with two, upper and lower X-direction guide shafts 13 on its side facing outward. Shown at 14 is an outer frame which is disposed at an end on the (Y, +) side and to which one end of each of Y-direction guide shafts 15, 15 is secured. The other end of each of the Y-direction guide shafts 15, 15 is secured to the back plate 12a of the frame 12. Between the frame 12 and the outer frame 14, a frame 16 is supported in a manner to freely slide relative to the Y-direction guide shafts 15, 15. Further, the frame 16 is provided with two, upper and lower X-direction guide shafts 17 on its side opposite to a back plate 16a thereof. Carrier bodies 18 and 19 are slidably supported by the X-direction guide shafts 13 and 17, respectively.

The carrier bodies 18 and 19 have tap arbors 20, 21 and 22, 23, respectively. An (X, −) side stopper 24 and and (X, +) side stopper 25 are provided at respective end parts of the X-direction guide shafts 13. Likewise, an (X, −) side stopper 26 and an (X, +) side stopper 27 are provided at respective end parts of the X-direction guide shafts 17. The mounting positions of the stoppers 24, 25, 26 and 27 are set so that the end port positions of the slender tubes 4, . . . mounted on the tube sheet 3, and the tap arbors 20 - 23 may correspond exactly.

Side plates 12b and 12c, mounted on opposite sides of the frame 12 are respectively provided with arms 28a and 28b. Appliances for an operation such as the inspection of the end ports of the slender tubes secured in the tube sheet 3 can be attached to fore end portions a and b of the respective arms 28a and 28b. The arms 28a and 28b can swivel by 180° within the plane of FIG. 3 about their base end portions c and d, respectively. Thus, the inspection work is made possible for all the slender tubes 4 on the (X, −) side and the slender tubes 4 on the (X, +) side of the device A. A first detector 29 is additionally provided at a side part of the carrier body 18 of the device A constructed as described above, while a second detector 30 and a third detector 31 at opposite side parts of the frame 16. The first detector 29 is adapted to detect when the device A comes close to the partition wall 5, while the second and third detectors 30 and 31 are adapted to detect when the device A comes close to the inside surface of the water chamber wall 1.

If, when it is to be attached to the tube plate 3 on the feed side 6 or the discharge side 7, the device A is attached symmetrically with respect to the partition wall 5, the second detector 30 mounted on the device A will detect the inner surface of the water chamber housing 1 at respective right or left bilateral positions as viewed in FIG. 1. Accordingly, assuming that the end ports of the closest slender tubes 4 to the points of intersection between the two walls 5 and 1 at which the first and second detectors 29 and 30 of the device a detect the partition wall 5 and the water chamber wall 1, respectively, are at $$\left\{ \begin{matrix} X & 1 \\ Y & 1 \end{matrix} \right\}$$

on the feed side 6 and at $$\left\{ \begin{matrix} X' & 1 \\ Y' & 1 \end{matrix} \right\}$$

on the discharge side 7, then $X = i$ corresponds to $X' = 93 - i$ and $Y = j$ corresponds to $Y' = j$ as regards an identical slender tube 4. That is, $$\left\{ \begin{matrix} X & i \\ Y & j \end{matrix} \right\} \text{and} \left\{ \begin{matrix} X' & 93-i \\ Y' & j \end{matrix} \right\}$$

represent the end ports at opposite ends of the same slender tube 4, so they can be changed to read. Assuming that, on the feed side 6, the end port of the slender tube 4 closest to the intersection point between the two walls 5 and 1 at which the first and second detectors 29 and 30 of the device A detect the partition wall 5 and water chamber wall 1 on the feed side 6, respectively, is at $$\left\{ \begin{matrix} X & 1 \\ Y & 1 \end{matrix} \right\},$$

and on the discharge side 7 that the end port of the slender tube 4 closest to the intersection point between the two walls 5 and 1 at which the first and third detectors 29 and 31 of the device A detect the partition wall 5 and water chamber wall 1 on the discharge side 7, respectively, is at $$\left\{ \begin{matrix} X' & 1 \\ Y' & 1 \end{matrix} \right\}, \text{then} \left\{ \begin{matrix} X & i \\ Y & j \end{matrix} \right\} \text{and} \left\{ \begin{matrix} X' & i \\ Y' & j \end{matrix} \right\}$$

represent the respective opposite end ports of the same slender tube 4. In this case, the reading direction needs to be reversed in the control of the device as based on the detection by the second detector 30 or the third detector 31.

The appliances for inspecting the slender tubes 4, which are respectively attached to the fore end portions a, b of the arms 28a, 28b, are well known as, for example, eddy current type detectors. As will be stated later, such eddy current type detector senses a defect of the slender tube 4 when the fore end of the detector is inserted into the tube 4 by means of a known driving device, not shown, at the stage at which the arm 28a or 28b is situated at the end port of the slender tube 4, for inspection, after the moving control of the device A.

Figure 6:
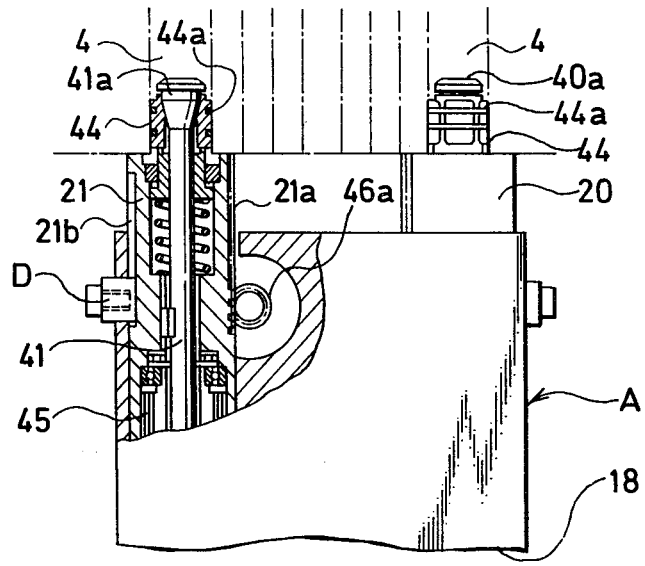
FIG. 6 is a conceptual side elevation, partially in vertical section, as viewed in the direction of line B — B in FIG. 5.
Figure 5:
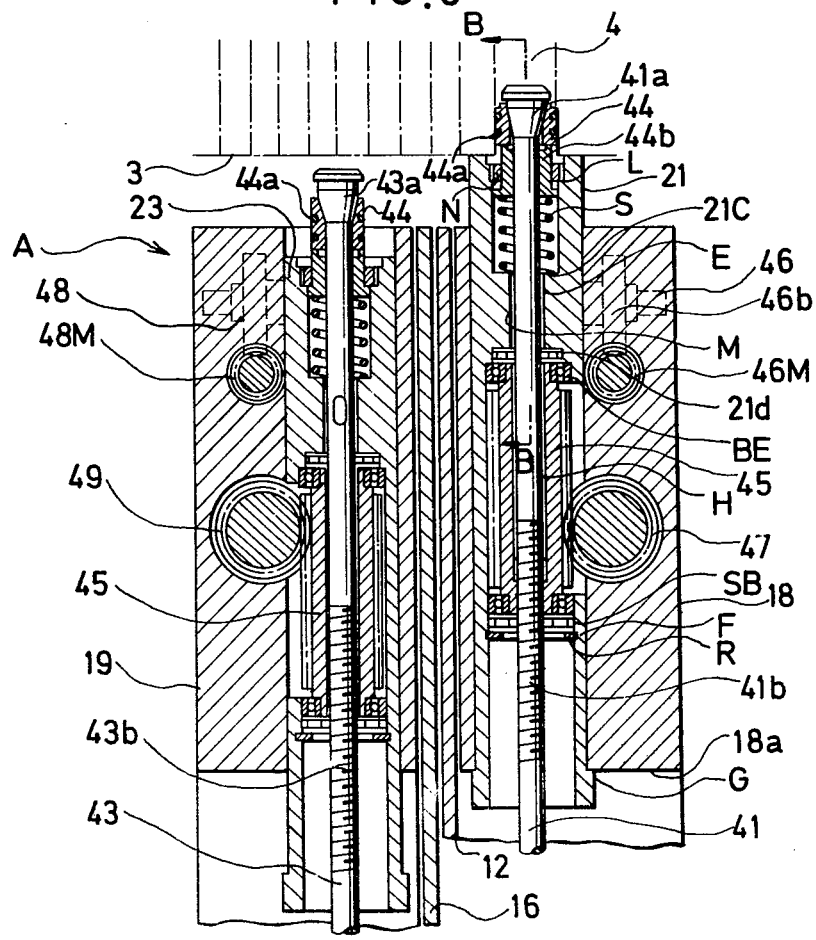
FIG. 5 is a conceptual vertical sectional side elevation as viewed in the direction of line A — A in FIG. 3.

In the case of the illustrated embodiment, the automatic inspection device A has its movement and stop control made automatically while being suspended from the slender tubes 4 by itself. FIGS. 5 and 6 show the conceptual internal structure of the device A for fulfilling the function as described above.

As shown in FIG. 6, an upper part of the tap arbor 21 is formed with a rack 21a for axially moving the tap arbor 21 up and down. A detent D for preventing the tap arbor 21 from turning is provided at an upper part of the carrier body 18, and its inner end is snugly fitted with a groove 21b of the tap arbor 21. Thus, the tap arbor 21 is supported so that it can slide freely only vertically relative to the carrier body 18. As illustrated in FIG. 5, a stepped portion E is provided and a key way M is formed inside the tap arbor 21. The upper surface 21c of the stepped portion becomes a seat for a compression spring S, while the lower surface 21d becomes a seat for a bearing BE. Outside the tap arbor 21, a stepped portion G is provided at a lower part. When the tap arbor 21 is raised, the stepped portion G abuts against the lower surface 18a of the carrier body 18 and serves as a raised end stopper of the tap arbor 21. When the tap arbor 21 is secured to the tube sheet 3, the stepped portion G supports the weight of the inspection device A.

Shown at 46 is a two-stage gear, the first stage gear of which is a pinion 46a (FIG. 6) meshing with the rack 21a of the tap arbor 21 and the second stage gear of which is formed with a worm wheel 46b meshing with a worm 46M. Although not shown, the two-stage gear shaft has both ends supported rotatably by bearings and is connected to a rotation driving source. The worm wheel 46b and the worm 46M are so constructed that the lead angle of the worm 46M is smaller than the friction angle in the meshing, and that whereas rotation can be transmitted from the worm 46M to the worm wheel 46b, it cannot be transmitted from the worm wheel 46b to the worm 46M.

In FIG. 5, numeral 47 denotes a skew gear of a driving system for driving a clamp bar 41 to thus clamp the device A onto the ceiling plate. Although not shown, the shaft of the skew gear has both the ends supported rotatably by bearings and is connected to a rotation driving source. Shown at 45 is a skew gear which meshes with the skew gear 47. Both ends of the skew gear 45 are rotatably supported by the tap arbor 21 through bearings. The upper end of the skew gear 45 is engaged with the stepped portion E of the tap arbor 21 through the thrust bearing BE, while the lower end is supported by a portion F through the seat for a lower-end thrust bearing SB as well as a snap ring R.

The tap arbor 21 and the skew gear 45 ascend and descend integrally in the axial direction. At this time, the skew gears 47 and 45 slip on the tooth surfaces thereof. The inner cylinder side of the skew gear 45 is formed with an internal thread H.

The clamp bar 41 is formed at a lower part with an external thread 41b, which meshes with the internal thread H of the skew gear 45. The clamp bar 41 has a key buried therein, which is engaged in the key way M of the tap arbor 21 and which is supported so as to be vertically slidable. The top of the clamp bar 41 has an expanded head 41a, which is formed with a guide taper so as to facilitate the insertion into the slender tube 4. The head 41a is also formed with a taper which fits with a jaw 44 of a collet.

When the skew gear 45 is rotated, the clamp bar 41 rotates and moves up and down by virtue of the female screw H of the skew gear 45.

The inner cylindrical surface of the jaw 44 of the collet is tapered, and is held in contact with the head 41a of the clamp bar 41. The jaw 44 of the collet can be separated into, for example, four parts, which are held by two expansion bands 44a so as to be prevented from being disjointed outwards. Shown at 44b is a housing of the jaw 44 of the collet. The housing 44b is formed with a hole which fits the collet jaw 44 therein in a manner to freely slide it only in the radial direction. The collet jaw is restrained in the thrust direction.

A step L is provided at a lower part of the housing 44b. When the clamp bar 41 is lowered relatively to the tap arbor 21, the housing 44b of the collet jaw 44 does not descend by virtue of the compression spring S. Owing to the elastic energy of the compression spring S, the device A can be stably supported on the tube plate 3 through the tap arbor 21.

Letter N indicates a nut whose outer periphery is threaded, and which is threadably engaged with a female screw of the tap arbor 21. The step portion L provided at a part of the housing 44b abuts against the nut L, thus to regulate the upward movement of the housing 44b. Thus, the elastic energy of the compression spring S is retained as the internal force of the tap arbor 21.

In FIGS. 5 and 6, no symbol is assigned to various constituent parts of the other tap arbors 20, 22 and 23 in order to clearly show the figures. Since, however, the respective constructions of the tap arbors and the clamp bars of the carrier bodies 18 and 19 are the same as in the foregoing, the details are omitted. In the figures, 40a designates the head of the clamp bar installed in the tap arbor 20, 43a the head of the clamp bar 43, 43b a male thread formed in the bar 43, 48 a two-stage gear, 48M a worm, and 49 a skew gear.

Description will now be made of a control system for the steam generator defect-detecting automaton constructed as stated above.

First of all, control elements for the control system will be explained. As will be stated later, the system has a switch for selecting the arm 28b or 28a. It is used as a change-over switch for selecting which of the job appliances, for the arms 28a and 28b is employed. The control system is provided with a command switch for swiveling the arm 28a or 28b leftwards or rightwards. Both arms 28a and 28b are automatically stopped at displacement from a mid-position of 90°, and have the displaced positions detected by limit switches. In this case, indicating lamps, which are activated by limit switches, indicate the swivel positions of the arms 28a and 28b.

Further, the system has a preset counter for commanding the address to which the device A is to be advanced, and an objective counter for indicating the present position of the device A. The system is also provided with a starting switch for starting the travel of the device A, and with operation end detecting switches, i.e., limit switches at all the limits of movement of the device A. Thus, the sequence control is conducted by confirming a signal regarding the operation of the device A. In addition, the system causes the objective counter to coincide with the present position by the use of the signal. Further, the system is provided with a 'misread' alarm for reporting missing of the present position when the objective counter has read erroneously, and with an origin reset switch for returning the device to $$\left\{ \begin{matrix} X & 1 \\ Y & 1 \end{matrix} \right\} \text{or} \left\{ \begin{matrix} X' & 1 \\ Y' & 1 \end{matrix} \right\}$$

to automatically stop it.

The selection of either of the two arms 28a and 28b of the device A, and the change of reading of the address during the swivel, are carried out as stated below. At the left and right ends of the device A, the appliances for the job, such as inspection, are attached to the fore end parts a and b of the arms 28a and 28b. The arms 28a and 28b can swivel through 180° to positions 90° from the mid-position, on the left and right outer sides of the device A, respectively. The stop positions at the displacements of 90° are detected by the limit switches. Thus, the job appliance mounted on the fore end part a of one arm 28a or that of the other arm 28b may be positioned so as to be aligned with the end port of the slender tube 4. Herein, the relation between the address of the tube plate 3 and the position at which the device A is attached is such that the position of the attachment is read in agreement with the address of the position at which the arm 28a or 28b is aligned with the end port of the slender tube 4. The control system changes to read the location of the device A by the swivel of the arms 28a and 28b and the selection of either the arm 28a or the arm 28b. Accordingly, the location of the device A directly represents the address of the slender tube 4 with which the job appliance is aligned.

As previously stated, the control system is provided with the two counters; the preset counter for commanding that address of the tube plate 3 at which the device A is to be brought to the end port of the slender tube 4, and the objective counter for indicating the actual position of the device A. Control is so made that the objective counter changes to read as the respective limits of the shifting operation of the device are being detected by the limit switches.

Where the objective counter is caused to coincide with the position of the device A at the beginning, the device A can be shifted from an arbitrary address to $$\left\{ \begin{matrix} X & 1 \\ Y & 1 \end{matrix} \right\} \text{or} \left\{ \begin{matrix} X' & 1 \\ Y' & 1 \end{matrix} \right\}$$

by the command of the origin reset switch. At this time, it is included as a requisite that the fore end part a of the arm 28a is infallibly swiveled to the position shown in FIG. 1.

Figure 8:
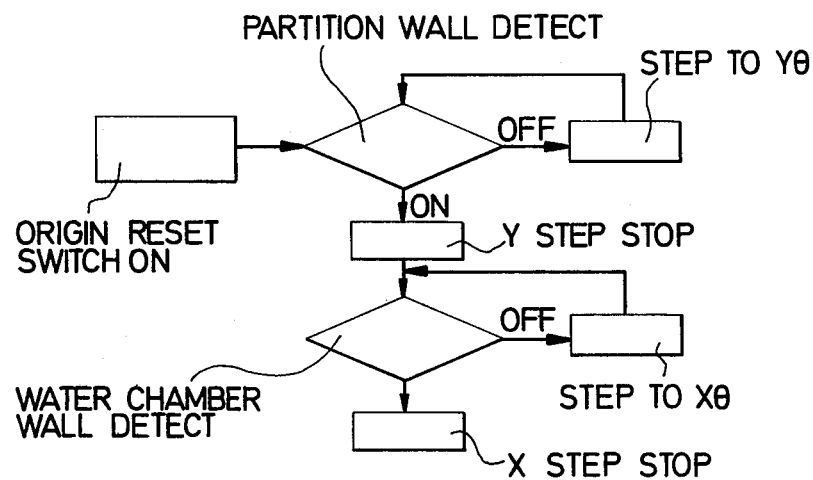
FIGS. 8 to 10 are block diagrams for explaining the method of controlling the automatic inspection device according to this invention.

As illustrated in FIG. 8, when the origin reset switch is turned "on," the device A shifts until the partition wall 5 and the water chamber wall 1 are detected by the first and second detectors 29 and 30. (At this time, for the sake of convenience, control is so made that the device shifts preferentially in the Y-direction and that, after detecting the partition wall 5, the device shifts in the X-direction until it detects the water chamber wall 1.) When the force end part a of the arm 28a is situated at $$\left\{ \begin{matrix} X & 1 \\ Y & 1 \end{matrix} \right\} \text{or} \left\{ \begin{matrix} X' & 1 \\ Y' & 1 \end{matrix} \right\},$$

the device A is automatically stopped. At this time, the indication of the objective counter is corrected to (1, 1).

Figure 9:
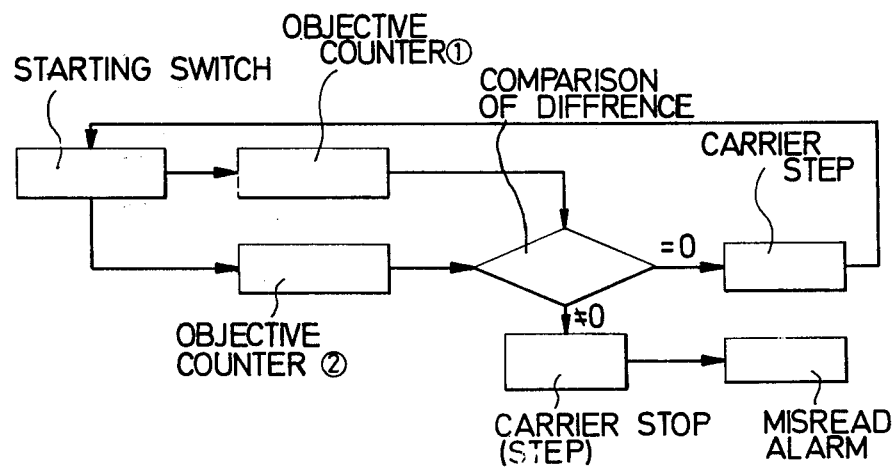

The detection of the misreading of the objective counter and the memory protection at the interruption of service will be explained with reference to FIG. 9. There are provided at least two channels of objective counters for indicating that address of the end port of the slender tube 4 mounted on the tube sheet 3 at which the device A is located. The objective counters count on the basis of signals of different sequences of the movement of the device A. When a difference occurs between the two channels of objective counters (In the normal condition, the contents of the objective counters are examined by reference when they coincide.), it is judged that the present position is missed. Then, the automatic stop is made, and the misreading is reported. One of the channels of the objective counters comprises a mechanical counter, which conserves the present position even at the service interruption.

Figure 10:
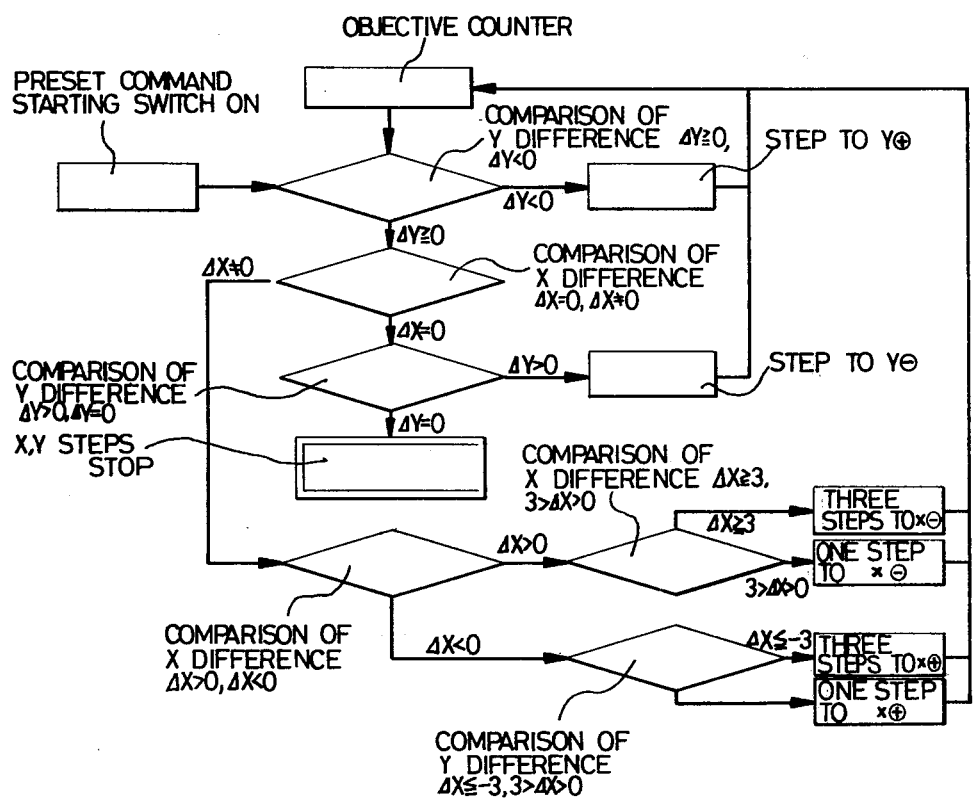

The relationship among the preset counter, the objective counter and the shift of the device A is as illustrated in FIG. 10. When it is desired to shift the device A to an arbitrary designated position, the designated position is set in the preset counter. When the starting switch is subsequently pushed, the device A is shifted in the direction of reducing the contents (or count) difference from the objective counter, indicating the present position, in the control system. The device A is so constructed that it can be shifted by one step or three steps in the X-direction. If the difference between the contents of both counters is three or more, the device A is shifted by three steps while, if the difference is one or two, the device is shifted by one step.

The tube sheet 3 is disk-shaped, and the steam generator has the partition wall 5 as well as the water chamber wall 1, so that the device A can strike against them. In order to shift the device A while avoiding such obstacle, control is made by determining the order of shift, as set forth below in this case.

Conditions on X or Y precedence. (Conditions in parentheses can be omitted from criteria.)

Assuming that the device shifts from $$\left\{ \begin{matrix} X & i_1 \\ Y & j_1 \end{matrix} \right\} \text{or} \left\{ \begin{matrix} X' & i_1 \\ Y' & j_1 \end{matrix} \right\} \text{to} \left\{ \begin{matrix} X & i_2 \\ Y & j_2 \end{matrix} \right\} \text{or} \left\{ \begin{matrix} X' & i_2 \\ Y' & j_2 \end{matrix} \right\},$$

then, when $(\Delta x = i_2 - i_1 \leqq 0)$ and $\Delta y = j_2 - j_1 < 0$, the shift of the device proceeds in the Y-direction while, when $(\Delta x = j_2 - j_1 \leqq 0)$ and $\Delta y = j_2 - j_1 \geqq 0$, it proceeds in the X-direction.

FIG. 7 is a view for conceptually explaining the driving system of the automatic inspection device A as is required in order to provide the above aspect of control. As will be described in detail hereunder, the carrier body 18 is controlled by the control system in cooperation with a driving motor $O_2$, magnetic clutches MC3 and MC4 and a plurality of limit switches for detecting the limits of movement of the device A. For a similar purpose, the carrier body 19 is provided with a driving motor $O_1$, magnetic clutches MC1, MC2, MC5 and MC7 and a plurality of limit switches. In FIG. 7, the same symbols as in FIGS. 3 to 6 represent the same parts or components. In the carrier body 18, a shaft 50, which has the worms 46M in order to simultaneously drive the tap arbors 20 and 21, is equipped with a gear $G_3$ and the magnetic clutch MC3 at one end part thereof. On the other hand, the clamp bars 40 and 41 are driven by the skew gears 47 meshing with the respective skew gears 45 as previously stated. The skew gears 47 are commonly installed on a shaft 51. At one end part of the shaft 51, there are a gear $G_4$, meshing with the gear $G_3$ of the shaft 50, and the magnetic clutch MC4. Here, the driving forces of the shafts 50 and 51 are transmitted from a two-stage gear $G_0$ which is slidably mounted on the X-direction guide shaft 13. The two-stage gear $G_0$ is directly coupled with the driving motor $O_2$ for the carrier body 18. The two-stage gear $G_0$ protrudes outside of the frame 12 with its hollow body penetrating through the carrier body 18 along the X-direction guide shaft 13, and it has a gear $G_0'$ at a terminal part thereof.

The means to move the carrier body 18 in the X-direction is a screw shaft 52 which has a gear $G_6$ meshing with the gear $G_0'$ and a magnetic clutch MC6. The screw shaft 52 penetrates through the frame 12 and is threadedly engaged in the carrier body 18 in parallel with the guide shaft 13.

On the other hand, the driving system of the carrier body 19 moves the body 19 in both the X- and Y-directions, and is therefore somewhat difference from that of the carrier body 18. Shafts 53 and 54, similar to the shafts 50 and 51, respectively provided for driving the tap arbors 22, 23 and the clamp bars 42, 43 are provided at first end thereof with respective gears $G_1$ and $G_2$ which mesh with each other. The coupling of the gears $G_1$ and $G_2$ is controlled by the respective magnetic clutches MC1 and MC2. The means to transmit a driving force to the gear $G_2$ consists of a two-stage gear $G_0$, which is installed on the X-direction guide shaft 17 of the body 19, and a motor $O_1$ which drives the gear $G_0$. Similarly to the construction in the case of the carrier body 18, the two-stage gear $G_0$ has its hollow body extending through the body 19 along the X-direction guide shaft 17 and possesses a gear $G_0'$ at a terminal part thereof. The gear $G_0'$ is coupled through an idle gear $G_a$ with a gear $G_7$ which is mounted on the X-direction guide shaft 17. The means to move the carrier body 19 in the X-direction consists of a screw shaft 55 equipped with a gear $G_5$ meshing with the gear $G_7$ and the magnetic clutches MC5 and MC7. The screw shaft 55 is threadedly engaged in the body 19 in the same manner as described above.

In order to move the carrier body 19 along the Y-direction guide shafts 15, 15, the frame 16 has screw shafts 56 and 57 at opposite ends parts thereof. Unlike the case of the carrier body 18, the X-direction guide shaft 17 of the carrier body 19 turns independently of the two-stage gears $G_0$ and $G_0'$. The turning force is transmitted to well-known worm coupling means attached to opposite ends of the shaft 17. The worm coupling means move the carrier body 19 along the Y-direction guide shafts 15, 15 in cooperation with the screw shafts 56 and 57.

The limits of movement of the carrier bodies 18 and 19 are appropriately detected by an arrangement of the limit switches as stated below.

The upper and lower limits of movement of the tap arbors 20, 21 and 22, 23 are detected by the limit switches LS1, LS2, LS5, LS6 and LS11, LS12, LS15, LS16. Among the limit switches, switches LS11 and LS12 belonging to the carrier body 18 detect the upper end and lower end of the tap arbors 20, 21, respectively, and switches LS15 and LS16 sense the safety of the upper-end movement in the arbors 20 and 21, respectively. The detecting operations of the limit switches LS1, LS2 and LS5, LS6 belonging to the carrier body 19 correspond to those of the limit switches LS11, LS12 and LS15, LS16, respectively. Here, when all the limit switches LS1, LS5 and LS6 are closed, the normal operations of the tap arbors 22 and 23 are detected. If, however, the limit switches LS5 and LS6 are closed during the open state of the limit switch LS1, it will be detected that the insertion of the tap arbors 22 and 23 into the slender tubes 4 is inferior. Then, the operation of the device A is emergency stopped, and a final clamp circuit to be described later is actuated. Such association of the limit switches applies also to the limit switches LS11 LS15 and LS16 of the carrier body 18. Among the magnetic clutches, clutches MC1 and MC3 regulate the drive of the tap arbors 22, 23 and 20, 21, respectively.

The limits of movement of the clamp bars 40, 41 and 42, 43 are detected by the limit switches LS3, LS4, LS7, LS8 and LS13, LS14, LS17, LS18. The limit switches LS13 and LS14, which belong to the carrier body 18 and which are arranged near the lower ends of the clamp bars 40 and 41, detect the unclamped states of the bars 40 and 41. The limit switches LS17 and LS18, which are arranged in proximity to the skew gears 47, detect the clamped states of the arbors 40 and 41. In the carrier body 19, the limit switches LS3, LS4 and LS7, LS8 correspond to the aspects of detection of the limit switches LS13, LS14 and LS17, LS18, respectively. Among the magnetic clutches, clutches MC2 and MC4 regulate the drive of the clamp bars 42, 43 and 40, 41, respectively.

The X-direction shift limits of the carrier body 18 are detected by the two limit switches LS19 and LS20 which are arranged on the back plate 12a of the frame 12. The limit switch LS19 detects the left advance end (X, −) of the body 18, while the limit switch LS20 detects the right advance end (X, +). The screw shaft 52 for the X-direction shift of the carrier body 18 is regulated by the magnetic clutch MC6.

Likewise, the X-direction shift limits of the carrier body 19 are detected by the limit switches LS9 and LS10, respectively. The limit switches LS24 and LS25 serve to detect the Y-direction shift ends of the body 19, and they sense the (Y, +) end and (Y, −) end, respectively. The screw shaft 55 for the X-direction shift of the body 19 has its drive regulated by the magnetic clutch MC5, while the rotation of the shaft 17 for the X-direction shift has its drive regulated by the magnetic clutch MC7.

On the other hand, the swivel limits of the arms 28a, 28b to the three positions are detected by the limit switches LS21a, LS22a, LS23a and LS21b, LS22b, LS23b, respectively. Here, the swivel drive of the arms 28a, 28b is executed by magnetic clutch brakes MC8a, MC8b which are installed at opposite ends of the X- direction guide shaft 13, and gear transmission means which cooperates therewith.

The control system for the automatic inspection device A as explained above is constructed as in FIG. 11 which shows an embodiment thereof in a block diagram. In the figure, numerals 60 and 61 designate the objective counter and the preset counter already explained, respectively. The objective counter 60 comprises two channels of electric counters 60A and 60B, and a magnetic counter 60C. The preset counter 61 is composed of a digital switch, and it feeds, to both the electric counters 60A and 60B, a set signal for giving a command position of the automatic inspection device A. Shown at 62 is a counter setting manual switch which is incorporated in a path for feeding the set signal. The magnetic counter 60C can be independently set by a counter set circuit 63 which is made up of a manual switch. In order to indicate the present position of the device A, the electric counters 60A and 60B provide indication outputs on an X-position display 65X and a Y-position display 65Y, respectively, through a change-over switch circuit 64. The electric counters 60A and 60B monitoring the present position of the device A are well-known up-down counters. The operation of the counters can be visually confirmed by an indicating lamp 67 for count error through a comparator 66 in order that the safe operation of the device A may be monitored.

In swiveling the arm 28a or 28b of the device A, a command is given to an output circuit 70 by the use of a manual control switch of an arm control circuit 68. The circuit 70 provides the objective counter 60 with three kinds of signals for swiveling the arm 28a or 28b through pitches of 90°. When the arm 28a or 28b is thus set at the 'right' position, 'center' position or 'left' position, the device A feeds a counter pulse to an input terminal 69. The pulse acts so as to change the value of the objective counter 60 through the output circuit 70.

Figure 13:
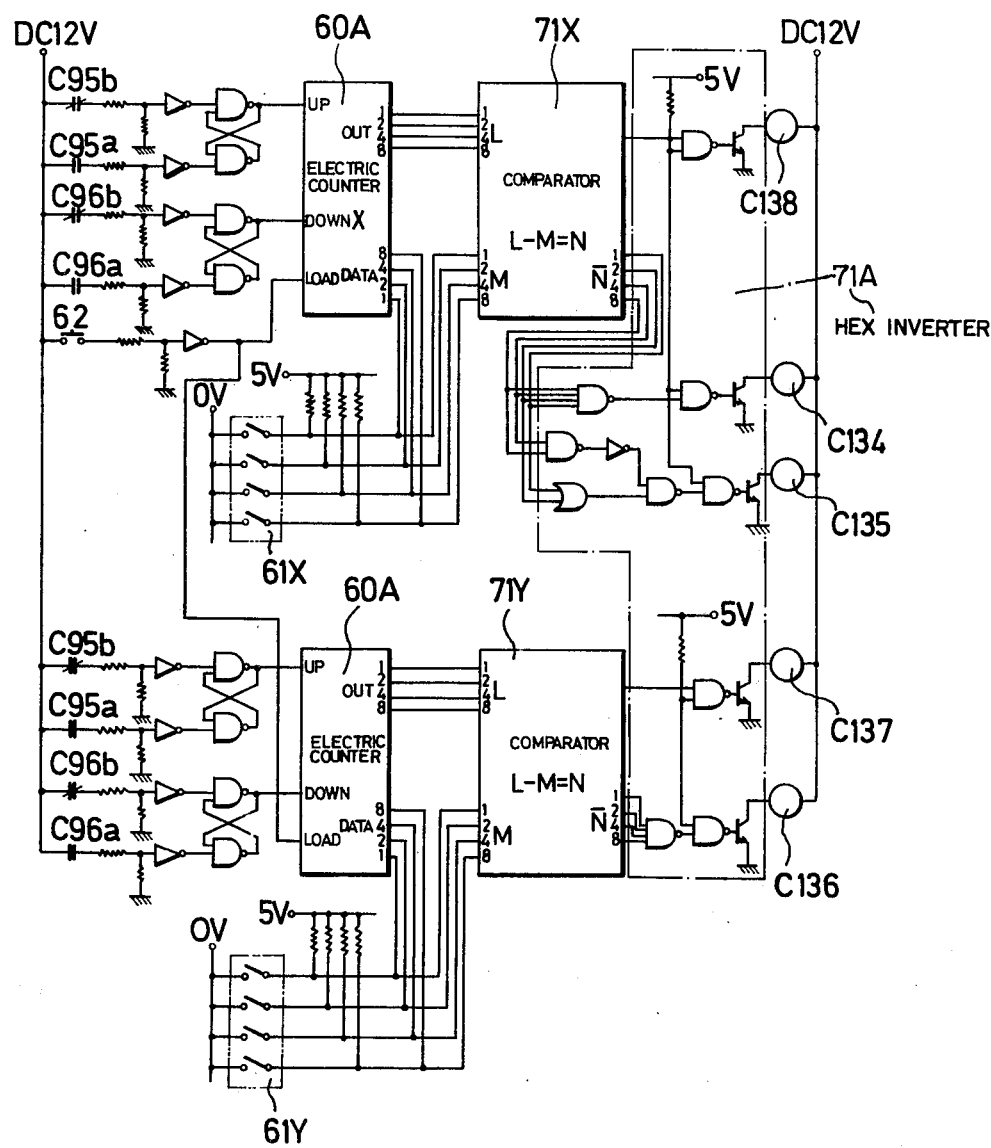
FIG. 13 is a circuit diagram showing an embodiment of an objective counter, a preset counter and an arithmetic circuit illustrated in FIG. 11.

The electric counter 60A, in the objective counter 60 and the preset counter 61 deliver respective inputs to an arithmetic circuit 71. The circuit 71 is composed of a comparator 71X which regulates the X-direction shift of the device A, and a comparator 71Y which regulates the Y-direction shift. A concrete example of the circuit 71 is shown in FIG. 13 along with the electric counters 60A and 60B in the objective counter 60. The arithmetic circuit 71 supplies an operation direction-discriminating circuit 72, disposed at the succeeding stage, with arithmetic or operation signals which are independent for the respective X- and Y-directions. The discriminator 72 gives the device A operation command signals finally through an operation condition output circuit 73. The main functions of the operation direction-discriminating circuit 72 are to judge the respective movement polarities of (X, +), (X, −), (X, O) and (Y, +), (Y, O), (Y, −) as regards the X-direction shift and Y-direction shift for the device A, and to discriminate whether or not the device is to be shifted every three steps (skipping over two slender tubes 4) in the (X, +) direction or (X, −) direction as regards the X-direction shift. As regards the Y-direction shift, (Y, +) or (Y, −) exclusively by one step is discriminated. As the result, the discriminator circuit 72 supplies the operation condition output circuit 73 with respectively different six signals. These signals consist of command signals (i) and (ii), for shifting the device three steps and one step in the (X, +) direction, respectively; command signals (iii) and (iv), the shifting the device three steps and one step in the (X, −) direction, respectively; and command signals (v) and (vi), for shifting the device one step in the (Y, +) direction and the (Y, −) direction, respectively.

The operation direction-discriminating circuit 72 is adapted to compare the command address M and the present address N. Consequently, device A reduces the value of Y when this is minus (−) and performs an operation in the direction X at that point in time when Y reaches zero. Additionally, circuit 72 compares X when Y is A or positive (+) and, as a result thereof, the mode of operation in the X direction (X one-step increased operation, X one-step decreased operation, X threestep increased operation and X three-step decreased operation) can be determined. At the point of time of completion of its operation (M−N)=O, the operation in the direction Y can be performed.

Figure 11:
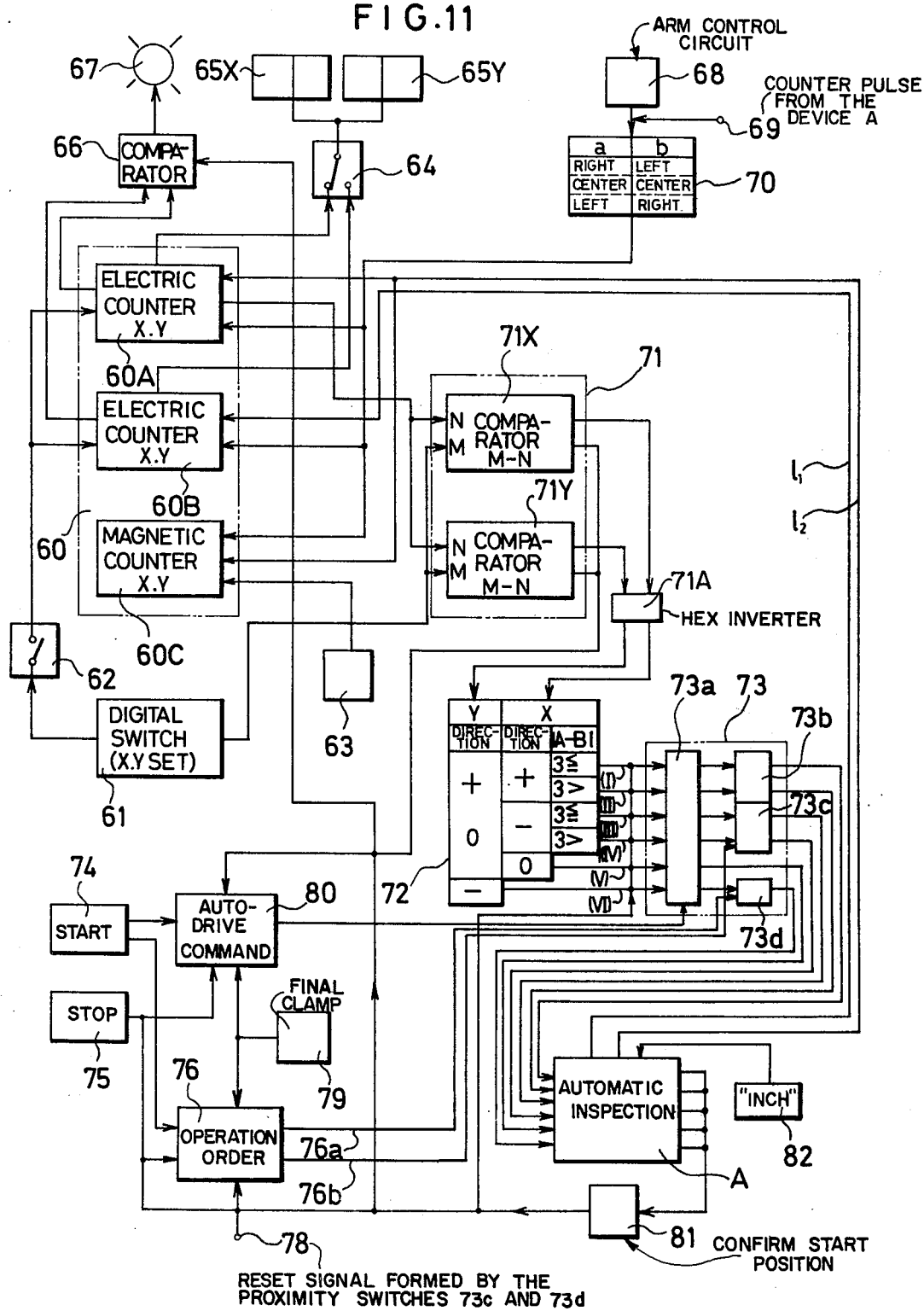
FIG. 11 is a block diagram showing the control system for the automatic inspection device according to this invention.

The operation condition output circuit 73 has an output confirmation circuit 73a, which receives any of the six signals (i) to (vi). Among the signals, the command signal (v) is directly delivered to the device A. The circuit 73 includes the detectors 29, 30 and 31 mounted on the device A as already explained. The detectors 29, 30 and 31 are constructed of proximity switches which are made up of known electromagnetic sensors etc. In FIG. 11, the detector 29 (for detecting the partition wall 5) is denoted by a proximity switch 73d, while the detectors 30 and 31 for detecting the wall of the water chamber 2 on the left and right sides are respectively denoted by proximity switches 73c and 73b. Accordingly, only in the case where the proximity switches 73b, 73c and 73d are in the "off" states (the state under which neither the partition wall 5 nor the water chamber housing on the left and right sides is detected), the command signals (i), (ii) and (iii), (iv), (vi) are transmitted to the device A.

The automatic inspection device A has its starting position confirmed by a circuit 81, which gives the starting position signal commonly to the respective input lines of the output confirming circuit 73a. The device A can perform an inching operation by the use of a manual control switch circuit 82. The automatic running and stop controls of the device A are performed by a start circuit 74 and a stop circuit 75, respectively. One output of the start circuit 74 is fed to a circuit 76 for determining the operation order of the device A. Thus, the circuit 76 feeds its outputs to the proximity switches 73d and 73c through lines 76a and 76b, respectively. The circuit 76 is so constructed as to provides four kinds of reset signals. Among the reset signals, two are received from the stop circuit 75 and the start position-confirming circuit 81. Another is a reset signal which is applied to a terminal 78. The reset signal received as the input to the terminal 78 is formed by the "on" states of both the proximity switches 73c and 73d. The last reset signal is given from the final clamp circuit 79 already referred to.

Numeral 80 denotes an auto-drive command circuit, which receives a set signal from the start circuit 74 and which can receive a reset signal from any of the arithmetic circuit 71, the stop circuit 75, the final clamp circuit 79 and the start position-confirming circuit 81. The output of the circuit 81 delivers the start position signal to a gate of the comparator 66, to monitor the operation of the objective counter 60. The device A delivers an 'up' or 'down' counter pulse, attendant upon the X-direction or Y-direction shift, to the objective counter 60 through lines $l_1$ or $l_2$. Here, the line $l_1$ is exclusively used for the electric counter 60B, while the line $l_2$ is a common input line to the counters 60A, 60B and 60C.

Counters 60A, 60B and 60C are provided in two channels of the objective counters for the purpose of receiving counter pulses, respectively, as mentioned above, and to compare the respective counter values of X and Y so that, when there is any error between them, an error signal or indication is provided, thus assuring a double safety procedure. Additionally, electric counter 60A and 60B and magnetic counter 60C concurrently serve to provide counter measures at a service interruption.

Description will now be made of the operation of the foregoing embodiment. It is supposed that, as shown in FIG. 1, the device A has been entered into the water chamber 2 on the feed side 6 from the feed side man way 10 and suspended in an arbitrary position on the tube sheet 3. First, the fore end part a of the arm 28a of the device A is adjusted to the position illustrated in FIG. 1 (that is, the closest position to the partition wall 5 among the three positions which the arm 28a can assume, or the position at which the fore end part a coincides with $$\begin{pmatrix} X & 1 \\ Y & 1 \end{pmatrix}$$

when the device A has detected the partition wall 5 and the water chamber wall 1). Subsequently, when the switch 62 for the return to the origin is turned "on," the device A shifts in the (Y, −) direction so that the first detector 29 (proximity switch 73d) detects the partition wall 5, and then shifts in the (X, −) direction so that the second detector 30 (proximity switch 73c) detects the water chamber wall 1. In consequence, the device A is automatically stopped. At this time, the device A is at the position at which the force end part a of the arm 28a corresponds to the address $$\begin{pmatrix} X & 1 \\ Y & 1 \end{pmatrix}$$

of the end port of the slender tube 4 mounted on the tube sheet 3. Therefore, the objective counter 60 is adjusted to $$\begin{pmatrix} X & 1 \\ Y & 1 \end{pmatrix}.$$

Subsequently, the preset counter 61 is set to a predetermined position $$\begin{pmatrix} X & i_1 \\ Y & j_1 \end{pmatrix},$$

and the start switch 74 is closed. Then, the device shifts to $X = i_1$ on the (X, +) side and subsequently to $Y = j_1$ on the (Y, +) side. At this time, the objective counter 60 sequentially changes to read by the signals of the limit switches at the limits of movement of the device A as the device A shifts. When the difference of the contents of the objective counter 60 from those of the preset counter 61 becomes (O, O), the device A stops automatically. In the shift process of the device A, the device can shift by single steps or by three steps in the X-direction. Therefore, if the difference between the preset counter 61 and the objective counter 60 is three or more, the device shifts by three steps while if the difference is one or two, the device shifts by single steps.

At the next stage, when the preset counter 61 is set to a predetermined position $$\begin{pmatrix} X & i_2 \\ Y & j_2 \end{pmatrix}$$

and the start switch 74 is closed, the device shifts in the ensuing order and automatically stops at $$\begin{pmatrix} X & i_2 \\ Y & j_2 \end{pmatrix}.$$

At $j_2 - j_1 < 0$, the device shifts preferentially in the Y-direction.

At $j_2 - j_1 \geq 0$, the device shifts preferentially in the X-direction.

In accordance with the selection of the arm 28a or 28b and the leftward or rightward swivel of the arm 28a or 28b, the objective counter 60 indicates the present position in terms of the position of the fore end a or b of the respective arm 28a or 28b. The address of the position for the work, such as inspection, can therefore be always confirmed. Such operation is similarly conducted on the discharge side 7.

Hereunder an example of the operation of the control system cooperating with the drive system of the automatic inspection device A will be explained with reference to FIGS. 12 and 13. The system sets the preset counter 61 in FIG. 11 to an arbitrary value, and executes the preset running through the start switch 74. As the condition of the running, the device A has confirmed, through the circuit 81, the fact that both the carrier bodies 18 and 19 clamp the slender tubes 4 and that the carrier body 19 is situated at the (X, −), (Y, −) end while the carrier body 18 is situated at the (X, +) end, and the fact that both the arms 28a and 28b lie at any of the respective three positions. If such condition is fulfilled, the device A is in the most stable positional state. Besides, the device A has its strongest resistance against the reaction force which arises in the defect inspection performed by attaching the inspection appliance for the slender tubes 4, e.g., the known eddy current detector to the arm 28a or 28b. Accordingly, the device A is controlled so as to fulfill the above state at both the initiation and termination of the running.

Figure 12:
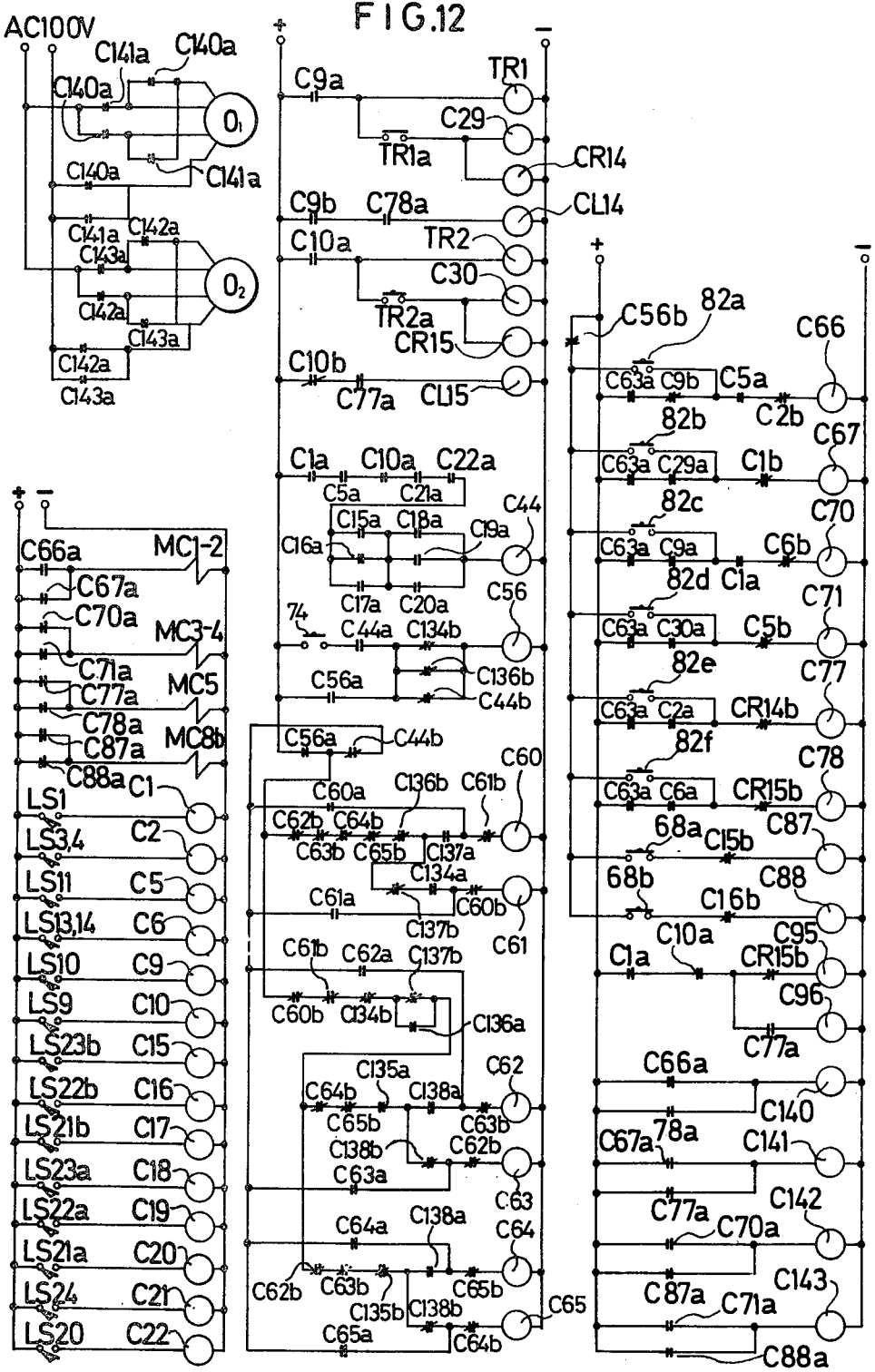
FIG. 12 is a sequence circuit diagram showing an example of a discriminator circuit in FIG. 11.

The above state of the device A is called the start position, which is confirmed by a relay C44 in FIG. 12. By depressing the start circuit 74 (switch) in the where the relay C44 is "on," a relay C56 is energized to close its a-contact c56a for self-holding, and the preset running is started. By way of example, let it be supposed that the objective counter 60 is at X = 1 and Y = 1 and that the preset counter 61 is set at X = 3 and Y = 2 by manipulating the digital switch thereof. This means that the X-side output of the electric counter 60A is "1" in the decimal number, which corresponds to "0001" in BCD. The X-side output of the preset counter 61 is decimal "3," which corresponds to "0011" in BCD. These outputs are applied to input ends N and M of an X-direction comparator 71X of the arithmetic circuit 71. Here, (M − N) is operated in a known aspect, and its sign and value are provided. In order to simplify the circuit arrangement of the succeeding stage, the output of the arithmetic circuit 71 is inverted by well-known means such as a hex inverter 71A, which concurrently serves the function of preventing erroneous action of the counter due to contact-point chattering. Therefore, the output of the comparator 71X becomes "1101" and the sign becomes minus H.

The relations between the output of the comparator 71X and relays C138, C134 and C135 in FIG. 13 will be discussed. The relay C138 is not energized when the output sign of the comparator 71X is minus H, whereas it is energized when the sign is 0 (zero) or plus. The relay C134 is energized only when the output value of the comparator 71X is "111" (decimal "0"). On the other hand, the relay C135 is energized only when the output value of the circuit 71X is "1101" or "1110". This indicates that, only when the difference between the present value of the electric counter 60A and the command value of the preset counter 61 is one or two, the relay C135 turns "on."

In FIG. 13, the relay C138 instructs the shift direction of the device A, and its "on" operation executes (X, −). The relay C134 is one for completion of the shift. The relay C135 is one for instructing the number of steps, and its "on" operation instructs one step while its "off" operation three steps. Similarly, a relay C137 in a Y-direction comparator 71Y serves to instruct the shift direction, and its "on" operation gives the (Y, −) instructions. C136 denotes an indicating relay for completion of the stepping.

The states of the relays corresponding to the X- and Y-directions will be studied in accordance with the above construction and on the above example of setting. As to the X-direction, the relays C138 and C134 are "off" and the relay C135 is "on." As to the Y-direction, both the relays C136 and C137 are "off."

Referring back to FIG. 12, relays C60 − C65 will be explained. Among the six relays, C60 instructs the operation of (Y,−) one step, C61 the operation of (Y, +) one step, C62 the operation of (X, −) one step, C63 the operation of (X, +) one step, C64 the operation of (X, −) three steps, and C65 the operation of (X, +) three steps. Due to the construction of an energizing circuit of the relay C60, the relay C60 conducts the "on" operation when all the relays C61 − C65 are "off," the relay C136 is "off" and both the relays C56 and C137 are "on." This signifies that the relay C60 turns "on" in case where, upon starting the preset running, the command address by the preset counter 61 is smaller than the present address by the electric counter 60B in the Y-direction. Likewise, Relay C61.....This conducts the "on" operation when the command address and the present address in the X-direction are equal, and besides, the command address is greater than the present address in the Y-direction.

Relay C62.....This conducts the "on" operation when the present address in the Y-direction is equal to or smaller than the command address and besides the present address in the X-direction differs from the command address, or when the differences of the addresses in both the directions are 1 or 2 and the present addresses are greater than the command addresses.

Relay C63.....This performs the "on" operation when the present address in the Y-direction is equal to or smaller than the command address and besides the present address in the X-direction differs from the command address, or when the differences of the addresses in both the directions are 1 or 2 and the present addresses are smaller than the command addresses.

Relay C64.....This performs the "on" operation when the present address in the Y-direction is equal to or smaller than the command address and besides the present address in the X-direction differs from the command address, or when the differences of the addresses in both the directions are neither 1 nor 2 and besides the present addresses are greater than the command addresses.

Relay C65.....This executes the "on" operation when the present address in the Y-direction is equal to or smaller than the command address and besides the present address in the X-direction differs from the command address, or when the differences of the addresses in both the directions are neither 1 nor 2 and besides the present addresses are smaller than the command addresses.

Naturally, interlock circuits are incorporated among the respective energizing circuits of the relays C60 − C65. Therefore, only one of the relays C60 − C65 operates at any time, and two or more of them operate simultaneously at no time.

In concluding the above explanation, the general relations of setting will be stated. Letting, generally, the present addresses be $(X = X_1, Y = Y_1)$ and the command addresses be $(X = X_2, Y = Y_2)$, the "on" operation conditions of the relays are indicated as follows:

"On" condition of C60: C56 "on" AND $Y_1 > Y_2$

"On" condition of C61: C56 "on" AND $Y_1 < Y_2$ AND $X_1 = X_2$

"On" condition of C62: C56 "on" AND $Y_1 \leq Y_2$ AND $X_1 - X_2 = 1$ OR $X_1 = X_2 = 2$ "On" condition of C63: C56 "on" AND $Y_1 \leq Y_2$ AND $X_1 - X_2 = -1$ OR $X_1 = X_2 = -2$ "On" condition of C64: C56 "on" AND $Y_1 \leq Y_2$ AND $X_1 - X_2 \neq 1$ OR $X_1 - X_2 \neq 2$ "On" condition of C65: C56 "on" AND $Y_1 \leq Y_2$ AND $X_1 - X_2 \neq -1$ OR $X_1 - X_2 \neq -2$ The "on" operations of the relays C60 − C65 correspond to the following operations of the device A:

C60 "on": (Y, −) one-step operation, C61 "on": (Y, +) one-step operation, C62 "on": (X, −) one-step operation, C63 "on": (X, +) one-step operation, C64 "on": (X, −) three-step operation, C65 "on": (X, +) three-step operation.

The reason why the device A is shifted in the aforecited directions is that the device is favorably moved without colliding against the housing 1 or the partition wall 5 in the steam generator of the specified type. In this regard, the present invention makes the control in such manner that, where the device A is to be shifted so as to decrease in the Y-direction (Y, −), the device A is firstly shifted to the command value in the Y-direction. On the contrary, where the device A is to be moved so as to increase in the Y-direction, the device A is shifted to the command value in the X-direction and thereafter to the command value in the Y-direction. Such order of the shifts in the X- and Y-directions can be arbitrarily altered in dependence on the configuration of the place for inspection, and safe shifting operations can be carried out.

On the basis of such control, the foregoing example of setting will be further explained. Now, the relay C138 in FIG. 13 is "off," C134 is "off," C135 is "on," C137 is "off," C136 is "off" and C56 is "on," so that the relay C63 becomes "on" and self-holding. Owing to the "on" state of the relay C63, the relay C66 turns "on" and C140 turns "on." The motor $O_1$ rotates normally and, simultaneously, the magnetic clutches MC1 and MC2 are energized. In consequence, the clamp bars 42 and 43 are driven upwards in FIG. 7, and the carrier body 19 falls into the unclamped state. Since the completion of this operation is detected by the limit switches LS3 and LS4, the relay C66 is turned "off" through the relay C2 at the time of completion. The relay C140 is therefore turned "off," to stop the motor $O_1$ and to deenergize the magnetic clutch MC2. Under this state, the whole device A is supported by the carrier body 18 only.

Subsequently, owing to the "on" state of the relay C2, the relay C77 turns "on." It turns the relay C141 "on," to rotate and drive the motor $O_1$ reversely and to simultaneously energize the magnetic clutch MC5. Therefore, the carrier body 19 is shifted by single steps in the (X, +) direction by the screw shaft 55. The completion of shift is detected by the limit switch LS10, so that the relay C9 turns "on" to actuate a timer relay TR1. After a predetermined delay time, the timer relay TR1 turns the relays CR14 and C29 "on." Therefore, the relay C77 is turned "off," the magnetic clutch MC5 is deenergized and the relay C67 is turned "on," whereby the motor $O_1$ is continually rotated and driven reversely. Since the relay C67 is "on," the magnetic clutch MC2 is energized again. When the clutch MC2 turns "on" owing to the reverse rotation of the motor $O_1$, the clamp mechanism of the carrier body 19 effects the clamp operation. This operation is continued until the limit switch for the clamp completion LS1 turns "on."

When the clamp of the body 19 is completed (C1 "on"), the relay C70 turns "on." Owing to the energization of the relay C70, the relay C142 turns "on," the motor $O_2$ of the body 18 rotates normally, and the clamping-unclamping clutches MC3, MC4 turn "on." When the motor $O_2$ rotates normally and the clutch MC4 is "on," the clamp mechanism on the side of the body 18 of the device A effects the unclamping operation. This operation is continued until the completion of unclamping (LS13 and LS14 "on"). Upon completion of the operation, the device A supports its own weight by only the clamp force of the body 19. The completion of the operation renders the relay C78 "on." Then, the relay C140 turns "on," the motor $O_1$ of the body 19 rotates normally, and the X-feeding clutch MC5 turns "on." When the motor $O_1$ rotates normally and the clutch MC5 is "on," the feed mechanism of the body 19 effects the leftward advance operation. In view of the relationship between the device A and the steam generator tube plate, the one-step leftward advance operation under this state under which the body 19 is clamped to the tube plate can be regarded as the leftward advance movement of the portion (including the arms) other than the stepping mechanism. As the result of this operation, the addresses of the arms 28a, 28b move by "1" rightwards (onto the + side). This operation turns the limit switch LS9 "on," and stops when CR15 turns "on" by the time-out of the energization of a timer relay TR2. At this time, C95 turns "on" during the time limit of the timer relay TR2. C95 supplies the counter 60A with "1"

up pulse. Flip-flops of this circuit prevent drawbacks ascribable to chattering of the relay contacts (as in a known circuit).

Owing to the "on" state of CR15 and C30, C70 turns "on." Owing to the "on" state of C70, C142 turns "on," the motor $O_2$ of the body 18 rotates normally, and the clamping-unclamping clutches MC3 and MC4 of the body 18 turn "on." When the motor $O_2$ rotates normally and the clutch MC4 is "on," the clamp mechanism of the body 18 of the device A performs the clamp operation. This operation stops when the clamp completion-confirming limit switch LS20 turns "on." Upon the closure of the limit switch LS20, one cycle of the (X, +) one-step operation is completed. When C44 turns "on," the self-holding of C63 is reset. However, even when the present address becomes (X = 2, Y = 1), "off" of C138, "off" of C34 and "on" of C135 do not change, and C63 remains "on." Accordingly, the next cycle of the (X, +) one-step operation is initiated. This cycle functions similarly to the preceding cycle, and it counts up the counter 60A by "1" in the X-value into (X − 3, Y = 1). Then, C134 turns "on." Upon completion of the cycle (C44 "on"), C63 turns "off" and C61 turns "on," and the (Y, +) one-step operation is initiated.

The circuit operation of the movement of the device A as based on the "on" state of C61 is the same in principle as the (X, +) one-step operation, and hence, the explanation is omitted. By the (Y, +) one-step operation, the Y-counter 60B counts up by "1," and C136 turns "on." When the start position is reached (C44 "on"), C56 is turned "off," and the preset running is stopped. The address at that time is (X = 3, Y = 2), which coincides with the value preset in the preset counter 61 (digital switches 61X, 61Y).

The reason why the operation of the arms 28a, 28b is required is that where, e.g., a guide mounted on the arm of the device A is to be held to the hole such as the tube 4 in the steam generator chamber, such is impossible with a fixed portion of the arm in some places. An example of operation to be stated hereunder refers only to the arm 28b, and the same principle applies to the arm 28a. When, under the state under which the arm 28b is not situated at the right swivel end (LS23b), the control switch 68b is depressed, C87 turns "on." Owing to the "on" state of C87, C142 turns "on," the motor $O_2$ rotates normally, and the arm swiveling clutch MC8b turns "on." When the motor $O_2$ rotates normally and the clutch MC8b turns "on," the arm 28b executes the rightward swivel operation. This operation can continue until the rightward swivel end-confirming limit switch LS28b turns "on." When the control switch 68a is depressed, the arm 28b executes the leftward swivel operation. This operation can continue until the limit switch LS21b turns "on."

Figure 14:
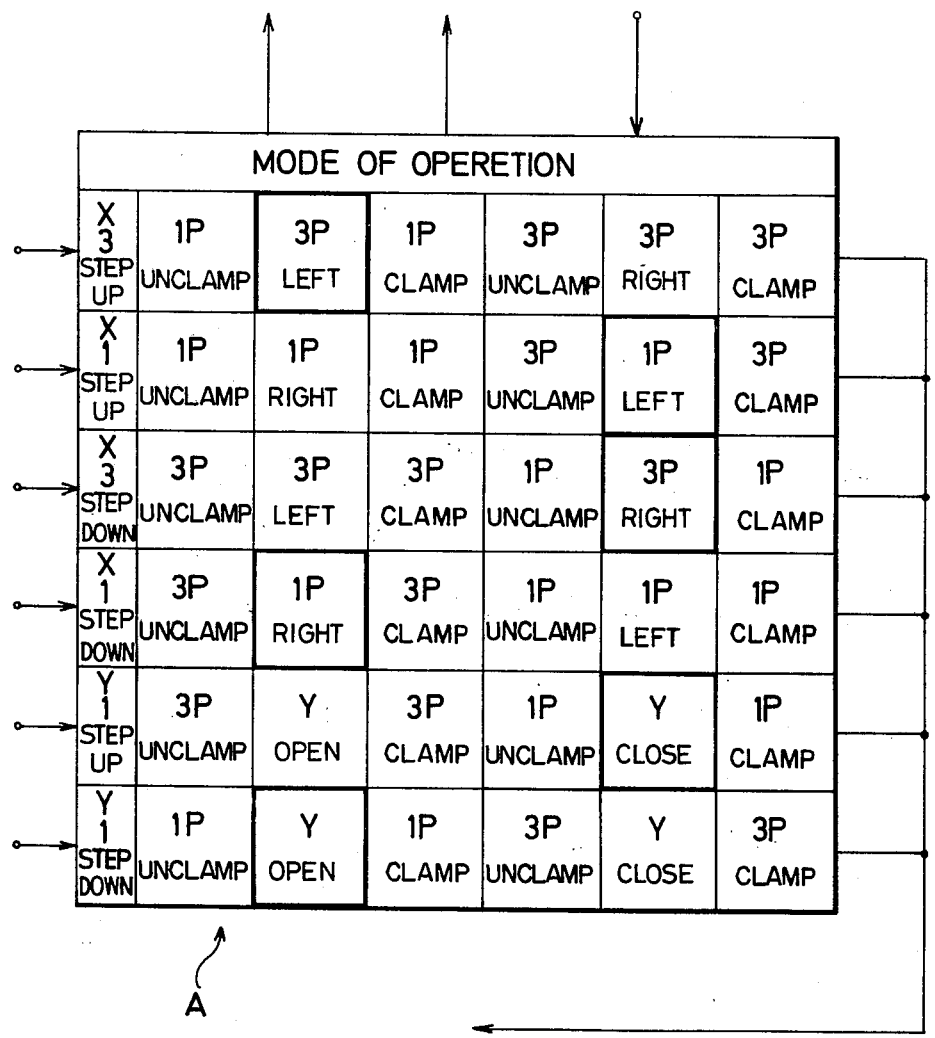
FIG. 14 is a diagram for explaining the operating mode of the automatic inspection device.

The arm operating circuit in FIG. 11 is associated with the arm 28b. Although the circuit of the arm 28a is not especially illustrated, it is the same as that of the arm 28b. In FIGS. 11 to 13, the same symbols indicate the same circuit elements. FIG. 14 illustrates the operating modes of the device A collectively. By the operations of blocks indicated by thick lines in FIG. 14, the position of the arm 28a or 28b is moved.

In FIG. 12, relays which have not been mentioned in the foregoing examples of operation are as follows. Relays C15 – C17 confirm the three positions of the arm 28b, while relays C18 – C20 conduct the same function for the arm 28a. Relays C21 and C22 confirm the operation limit in the (Y, −) direction and the operation limit to which the device is shifted in the (X, +) direction every three steps. A relay C71 is one for the clamp of the carrier body 18, a relay C88 is one for the leftward swivel operation of the arm 28b, a relay C96 is one for supplying a "1 down" counter pulse to the objective counter 60, and a relay C143 is one for the reverse rotation drive of the motor O$_2$. Manual switches 82a – 82f assembled in respective energizing circuits of the relays C66, C67, C70, C71, C77 and C78 are provided for inching in the circuit 82. Normally-open contacts and normally-closed contacts of the respective relays are indicated by a and b, respectively.

Although, in the foregoing embodiment, the description has been directed to the method of controlling the steam generator defect-detecting automaton and the apparatus therefor, this invention can also be adopted in the automated control method for machining (such as drilling, boring, tapping, punching, grinding, polishing, cleaning, coating, lining, and painting).

As set forth above, according to this invention, addresses are assigned to alignment holes; the location of a device is indicated on an objective counter in terms of the address, while a preset counter for instructing the shifting direction of the device in terms of the address is provided; when instructions are given to the preset counter, they are compared with the contents of the objective counter, whereupon the device is shifted in the direction of reducing the difference resultant from the comparison; and the device is provided with a detector for detecting an obstacle so as to shift avoiding the obstacle; so that the device can be controlled remotely and automatically, and that the location of the device can be confirmed. Accordingly, even in the case where a large number of holes such as slender tubes in a water chamber of a steam generator are individually inspected, the work can be efficiently executed.

What is claimed is:

1. A method of controlling positioning of an automatic inspection device, arranged to be installed in a field of alignment holes and shifted by using the alignment holes, and which device has a frame, a first carrier body mounted on said frame for shifting in an X-direction, a second carrier body mounted on said frame for shifting in mutually perpendicular X-Y-directions, clamping means on both carrier bodies clampingly engageable in the alignment holes, arm means pivoted on said second carrier body and having a free end for mounting an inspection means, and obstacle detection means: said method comprising the steps of assigning respective X-Y addresses to the alignment holes; indicating, on an objective counter in terms of its address, the location of said automatic inspection device; providing a preset counter for instructing the shifting direction of said device in terms of an address to which said device is to be moved; responsive to supplying instructions to said preset counter, comparing the address of such instructions with the address contents of said objective counter; responsive to such comparison, shifting said device in a direction to reduce the difference resulting from such comparison; and, during such shifting, utilizing said obstacle detection means to avoid any obstacles in the shifting path of said device.

2. A method, as defined in claim 1, including the step of controllably pivoting said arm means to bring the free end thereof into alignment with a hole to be inspected.

3. A method, as defined in claim 1, including the step of controlling the shifting of said device in the X-direction to shift by either single steps or by three steps.

4. A method, as defined in claim 3, controlling the shifting of said device in the X-direction to shift by a distance of three steps when the count differs between the preset counter and the objective counter is at least three, and to shift by one step in the X-direction when such count difference is less than three.

5. A method, as defined in claim 1, including the steps of in a first state, prior to initiation of a preset running of said automatic inspection device, and in a second state, at the termination of said preset running of said automatic inspection device, utilizing said clamping means to clamp said automatic inspection device to said holes; confirming that, in both said first and second states, said second carrier body is situated at an (X−) and (Y−) limit of its movement and said first carrier body is situated at the (X+) limit of its movement; and confirming that said arm means are pivoted to a respective one of three angular positions.

6. A method, as defined in claim 1, including the step of, when said automatic inspection device is to be shifted so as to decrease in a Y-direction, initially shifting said automatic respective device, responsive to an instruction value, in said Y-direction; and, when conversely, said automatic inspection device is to be shifted so as to increase in said Y-direction, said automatic inspection device is initially shifted, responsive to an instruction value, in an X-direction and thereafter shifted, responsive to the instruction value, in said Y-direction.

7. A method, as defined in claim 1, including the step of providing two channels of objective counters; and, responsive to a difference arising between the respective count values of the two channels of objective counters, stopping the shifting of said automatic inspection device on the basis that said device has missed the selected position.

8. A method, as defined in claim 7, including the step of conserving the then position of said automatic inspection device by one of said two channels of objective counters.

9. A method, as defined in claim 1, in which, when the instruction address is smaller than the present address in the Y-direction, said automatic inspection device is shifted by single steps in the (Y−) direction; when the instruction address and the present address, in an X-direction, are equal, and when the instruction address is greater than the present address in the Y-direction, said device is shifted by single steps in a (Y,+) direction; when the present address in the Y-direction is equal to or smaller than the instruction address and, when the present address in the X-direction differs from the instruction address, or when the differences between the addresses in both directions are less than three and the present addresses are greater than the instruction addresses, said device is shifted by single steps in an (X) direction; when the present address in the Y-direction is equal to or smaller than the instruction address and the present address in the X-direction differs from the instruction address, or where the differences between the addresses in both directions are less than three and the present addresses are smaller than the instruction addresses, said device is shifted by single steps in an (X,+) direction; when the present address in the Y-direction is equal to or smaller than the instruction address and when the present address in the X-direction differs from the instruction address, or where the differences between the addresses in both directions are in excess of two and the present addresses are greater than the instruction addresses, said device is shifted by three steps in the (X,−) direction; and when the present address in the Y-direction is equal to or smaller than the instruction address and the present address in the X-direction differs from the instruction address, or where the differences between the addresses in both directions are greater than two and the present addresses are smaller than the instruction addresses, said device is shifted by three steps from the (X,+) direction.

10. A control system for an automatic inspection device, arranged to be installed in a field of alignment holes having respective addresses defined by coordinates in mutually perpendicular X- and Y- directions, and operable to align an inspection means with a selected hole, said device including a frame, a first carrier body mounted on said frame for shifting in the X-direction, a second carrier body mounted on said frame for shifting in both the X- and Y- directions, and a pair of arms each pivotally mounted on said second carrier body and having a free end for mounting an inspection means; said control system comprising, in combination, at least one objective counter operable to indicate the address of the initial position of said automatic inspection device; a preset counter for setting an address, in a shifting direction of said device, in order to move said device to a desired position; and an arithmetic circuit operable to compare the counts of said objective counter and said preset counters for movement of said device in a direction effective to reduce the count difference resulting from such comparison.

11. A control system as defined in claim 10, including a stage succeeding said arithmetic circuit; said stage including an operation direction-discriminating circuit, for determining the shifting direction of said automatic inspection device, and a stepping unit for the shifting movement.

12. A control system, as defined in claim 10, including an output circuit providing a final operation instruction signal for said automatic inspection device.

13. A control system, as defined in claim 12, including a start-stop circuit for providing a preset running of said automatic inspection device; an auto-drive command circuit operable to supply said output circuit with a running instruction signal; and an arm operating circuit supplying said objective counter with an instruction signal to selectively pivot both arms of said device to selected angular positions.

14. A control system, as defined in claim 10, in which said system includes two juxtaposed up-down electric counters as said objective counter; said preset counter comprising a digital switch; said arithmetic circuit comprising comparators operable to make the comparisons in the X- and Y- directions independently.

15. A control system, as defined in claim 14, including a hex inverter connected to said arithmetic circuit and operable to invert an output of said arithmetic circuit.

16. The control system, as defined in claim 28, in which said operation direction-discriminating circuit comprises a relay sequence control circuit cooperating with said arithmetic circuit.

17. A control system, as defined in claim 11, in which said automatic inspection device includes respective motors for individually driving said carrier bodies; a plurality of groups of limit switches operable to detect the limits of movement of said carrier bodies; and magnetic clutches interposed between the respective motors and driving shafts for said carrier bodies for transmitting power to said driving shafts; said magnetic clutches being operatively associated with said motors and said limit switches under control of said operation direction-discriminating circuit.

* * * * *